(12) United States Patent
Jordan et al.

(10) Patent No.: US 8,337,543 B2
(45) Date of Patent: Dec. 25, 2012

(54) PROSTHESIS ANCHORING AND DEPLOYING DEVICE

(75) Inventors: Gary Jordan, Litchfield, NH (US);
Gary J. Leanna, Holden, MA (US);
Dean Molloy, Kilrush Hollymount (IE);
Paul K. Norton, Lunenburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 494 days.

(21) Appl. No.: 10/982,465

(22) Filed: Nov. 5, 2004

(65) Prior Publication Data

US 2006/0100688 A1 May 11, 2006

(51) Int. Cl.
*A61F 2/06* (2006.01)
(52) U.S. Cl. .................................. 623/1.12; 623/1.53
(58) Field of Classification Search .............. 604/93.01, 604/96.01; 623/1.11–1.35, 1.49–1.54; 606/194, 606/108, 195, 200
See application file for complete search history.

(56) References Cited

U.S. PATENT DOCUMENTS

| | | | |
|---|---|---|---|
| 4,300,244 A | 11/1981 | Bokros | 3/1.4 |
| 4,512,338 A | 4/1985 | Balko et al. | 128/1 R |
| 4,553,545 A | 11/1985 | Maass et al. | 128/341 |
| 4,572,186 A | 2/1986 | Gould et al. | 128/341 |
| 4,580,568 A | 4/1986 | Gianturco | 128/345 |
| 4,665,771 A | 5/1987 | Mitchell | 74/788 |
| 4,665,918 A | 5/1987 | Garza et al. | 128/343 |
| 4,681,110 A | 7/1987 | Wiktor | 128/343 |
| 4,732,152 A | 3/1988 | Wallsten et al. | 128/343 |
| 4,733,665 A | 3/1988 | Palmaz | 128/343 |
| 4,740,207 A | 4/1988 | Kreamer | 128/325 |
| 4,762,128 A | 8/1988 | Rosenbluth | 128/343 |
| 4,768,507 A | 9/1988 | Fischell et al. | 128/303 |
| 4,795,458 A | 1/1989 | Regan | 623/1 |
| 4,830,003 A | 5/1989 | Wolff et al. | 128/343 |
| 4,848,343 A | 7/1989 | Wallsten et al. | 128/343 |
| 4,875,480 A | 10/1989 | Imbert | 128/343 |
| 4,878,906 A | 11/1989 | Lindemann et al. | 623/1 |
| 4,886,062 A | 12/1989 | Wiktor | 128/343 |
| 4,893,623 A | 1/1990 | Rosenbluth | 606/192 |
| 4,907,336 A | 3/1990 | Gianturco | 29/515 |
| 4,913,141 A | 4/1990 | Hillstead | 606/108 |
| 4,950,227 A | 8/1990 | Savin et al. | 604/8 |
| 4,969,458 A | 11/1990 | Wiktor | 604/194 |
| 4,969,890 A | 11/1990 | Sugita et al. | 606/192 |
| 4,990,155 A | 2/1991 | Wilkoff | 606/191 |
| 4,998,539 A | 3/1991 | Delsanti | 128/898 |

(Continued)

FOREIGN PATENT DOCUMENTS

EP 0819411 1/1998

(Continued)

*Primary Examiner* — Kathleen Sonnett
(74) *Attorney, Agent, or Firm* — Vidas, Arrett and Steinkraus

(57) ABSTRACT

A system for intraluminally delivering and deploying stents and other prostheses includes an outer catheter, an inner catheter movable axially relative to the outer catheter, and an anchoring device mounted to a distal end region of the inner catheter. The anchoring device includes one or more control features that interact with a linking structure proximally disposed on the prosthesis, preferably including one or more loops. The control features and loops interact by surface engagement to anchor the prosthesis relative to the inner catheter in a nonfrictional manner, thus to maintain lower axial prosthesis deployment and retraction forces. In one version of the anchor, the control features extend radially outward from a sleeve. In another version, the control features are formed in respective recesses which also receive the loops or other linking structure.

19 Claims, 5 Drawing Sheets

U.S. PATENT DOCUMENTS

| | | | |
|---|---|---|---|
| 5,002,560 A | 3/1991 | Machold et al. | 606/198 |
| 5,026,377 A | 6/1991 | Burton et al. | 606/108 |
| 5,034,001 A | 7/1991 | Garrison et al. | 604/53 |
| 5,035,706 A | 7/1991 | Giantureo et al. | 604/198 |
| 5,037,392 A | 8/1991 | Hillstead | 604/96 |
| 5,037,427 A | 8/1991 | Harada et al. | 606/108 |
| 5,041,126 A | 8/1991 | Gianturco | 606/195 |
| 5,059,166 A | 10/1991 | Fischell et al. | 600/3 |
| 5,061,275 A | 10/1991 | Wallsten et al. | 623/1 |
| 5,064,435 A | 11/1991 | Porter | 623/12 |
| 5,071,407 A | 12/1991 | Termin et al. | 604/104 |
| 5,078,720 A | 1/1992 | Burton et al. | 606/108 |
| 5,089,005 A | 2/1992 | Harada | 606/194 |
| 5,089,006 A | 2/1992 | Stiles | 606/198 |
| 5,092,877 A | 3/1992 | Pinchuk | 623/1 |
| 5,108,416 A | 4/1992 | Ryan et al. | 606/194 |
| 5,123,917 A | 6/1992 | Lee | |
| 5,135,517 A | 8/1992 | McCoy | 604/281 |
| 5,158,548 A | 10/1992 | Lau et al. | 604/96 |
| 5,163,952 A | 11/1992 | Froix | 623/1 |
| 5,163,958 A | 11/1992 | Pinchuk | 623/11 |
| 5,171,262 A | 12/1992 | MacGregor | 623/1 |
| 5,183,085 A | 2/1993 | Timmermans | 140/89 |
| 5,192,297 A | 3/1993 | Hull | 606/195 |
| 5,197,978 A | 3/1993 | Hess | 623/1 |
| 5,201,757 A | 4/1993 | Heyn et al. | 606/198 |
| 5,222,969 A | 6/1993 | Gillis | 606/194 |
| 5,222,971 A | 6/1993 | Willard et al. | 606/158 |
| 5,226,913 A | 7/1993 | Pinchuk | 623/1 |
| 5,234,457 A | 8/1993 | Andersen | 606/198 |
| 5,242,451 A | 9/1993 | Harada et al. | 606/108 |
| 5,256,146 A | 10/1993 | Ensminger et al. | 604/104 |
| 5,258,020 A | 11/1993 | Froix | 623/1 |
| 5,258,098 A | 11/1993 | Wagner et al. | 606/108 |
| 5,263,964 A | 11/1993 | Purdy | 606/200 |
| 5,282,823 A | 2/1994 | Schwartz et al. | 606/198 |
| 5,282,824 A | 2/1994 | Gianturco | 606/198 |
| 5,290,295 A | 3/1994 | Querals et al. | 606/108 |
| 5,304,200 A | 4/1994 | Spaulding | 606/198 |
| 5,306,294 A | 4/1994 | Winston et al. | 623/1 |
| 5,354,308 A * | 10/1994 | Simon et al. | 623/1.15 |
| 5,354,309 A | 10/1994 | Schnepp-Pesch et al. | 606/198 |
| 5,372,600 A | 12/1994 | Beyar et al. | 606/108 |
| 5,378,239 A | 1/1995 | Termin et al. | 604/104 |
| 5,395,390 A | 3/1995 | Simon et al. | 606/198 |
| 5,403,341 A | 4/1995 | Solar | 606/198 |
| 5,405,377 A | 4/1995 | Cragg | 623/1 |
| 5,411,507 A | 5/1995 | Heckele | 606/108 |
| 5,411,552 A | 5/1995 | Andersen et al. | 623/2 |
| 5,415,664 A | 5/1995 | Pinchuk | 606/108 |
| 5,443,496 A | 8/1995 | Schwartz et al. | 623/1 |
| 5,453,090 A | 9/1995 | Martinez et al. | 604/53 |
| 5,456,694 A | 10/1995 | Marin et al. | 606/198 |
| 5,474,563 A * | 12/1995 | Myler et al. | 606/108 |
| 5,478,349 A | 12/1995 | Nicholas | 606/198 |
| 5,484,444 A | 1/1996 | Braunschweiler et al. | 606/108 |
| 5,496,277 A | 3/1996 | Termin et al. | 604/104 |
| 5,507,771 A | 4/1996 | Gianturco | 606/198 |
| 5,522,883 A | 6/1996 | Slater et al. | 623/1 |
| 5,534,007 A | 7/1996 | St. Germain et al. | 606/108 |
| 5,554,181 A | 9/1996 | Das | 623/1 |
| 5,576,006 A | 11/1996 | Smith | 623/1.11 |
| 5,591,230 A | 1/1997 | Horn et al. | 623/1 |
| 5,690,643 A | 11/1997 | Wijay | 606/108 |
| 5,702,364 A | 12/1997 | Euteneuer et al. | 606/96 |
| 5,702,418 A | 12/1997 | Ravenscroft | |
| 5,716,393 A | 2/1998 | Lindenberg et al. | 623/1 |
| 5,733,325 A | 3/1998 | Robinson et al. | |
| 5,772,669 A | 6/1998 | Vrba | 606/108 |
| 5,797,952 A | 8/1998 | Klein | |
| 5,800,519 A | 9/1998 | Sandock | 623/1 |
| 5,807,327 A | 9/1998 | Green et al. | 604/96 |
| 5,817,102 A | 10/1998 | Johnson et al. | |
| 5,824,041 A * | 10/1998 | Lenker et al. | 606/195 |
| 5,833,707 A | 11/1998 | McIntyre et al. | 606/198 |
| 5,836,965 A * | 11/1998 | Jendersee et al. | 623/1.11 |
| 5,935,135 A * | 8/1999 | Bramfitt et al. | 623/1.11 |
| 5,935,161 A * | 8/1999 | Robinson et al. | 128/898 |
| 5,948,017 A | 9/1999 | Taheri | 623/1 |
| 5,954,729 A | 9/1999 | Bachmann et al. | 606/108 |
| 6,001,123 A | 12/1999 | Lau | 623/1 |
| 6,007,574 A | 12/1999 | Pulnev et al. | 623/1 |
| 6,017,362 A | 1/2000 | Lau | 623/1 |
| 6,027,529 A * | 2/2000 | Roychowdhury et al. | 623/1.53 |
| 6,053,941 A | 4/2000 | Lindenberg et al. | 623/1 |
| 6,077,295 A | 6/2000 | Limon et al. | 623/1 |
| 6,102,940 A | 8/2000 | Robichon et al. | 623/1 |
| 6,120,522 A * | 9/2000 | Vrba et al. | 606/190 |
| 6,241,757 B1 | 6/2001 | An et al. | 623/1.1 |
| 6,258,099 B1 * | 7/2001 | Mareiro et al. | 606/108 |
| 6,264,689 B1 | 7/2001 | Colgan et al. | 623/1.22 |
| 6,302,893 B1 | 10/2001 | Limon et al. | 606/1.08 |
| 6,309,415 B1 | 10/2001 | Pulnev et al. | 623/1.22 |
| 6,350,278 B1 | 2/2002 | Lenker et al. | |
| 6,352,553 B1 | 3/2002 | van der Burg et al. | 623/1.23 |
| 6,419,694 B1 | 7/2002 | Sandock | 623/1.22 |
| 6,468,301 B1 | 10/2002 | Amplatz et al. | 623/1.13 |
| 6,514,282 B1 | 2/2003 | Inoue | 623/1.13 |
| 6,520,983 B1 | 2/2003 | Colgan et al. | |
| 6,585,758 B1 * | 7/2003 | Chouinard et al. | 623/1.16 |
| 6,607,551 B1 * | 8/2003 | Sullivan et al. | 623/1.11 |
| 6,623,518 B2 | 9/2003 | Thompson et al. | 623/1.11 |
| 6,641,608 B1 | 11/2003 | Pulnev | 623/1.15 |
| 7,172,617 B2 * | 2/2007 | Colgan et al. | 623/1.11 |
| 7,517,361 B1 | 4/2009 | Ravenscroft | |
| 7,655,039 B2 | 2/2010 | Leanna et al. | |
| 2001/0007082 A1 | 7/2001 | Dusbabek et al. | 623/1.11 |
| 2003/0040771 A1 * | 2/2003 | Hyodoh et al. | 606/200 |
| 2003/0040789 A1 * | 2/2003 | Colgan et al. | 623/1.11 |
| 2004/0204749 A1 | 10/2004 | Gunderson | |
| 2009/0177264 A1 | 7/2009 | Ravenscroft | |

FOREIGN PATENT DOCUMENTS

| | | |
|---|---|---|
| JP | 9173469 | 7/1997 |
| WO | 02/07795 | 1/2002 |

* cited by examiner

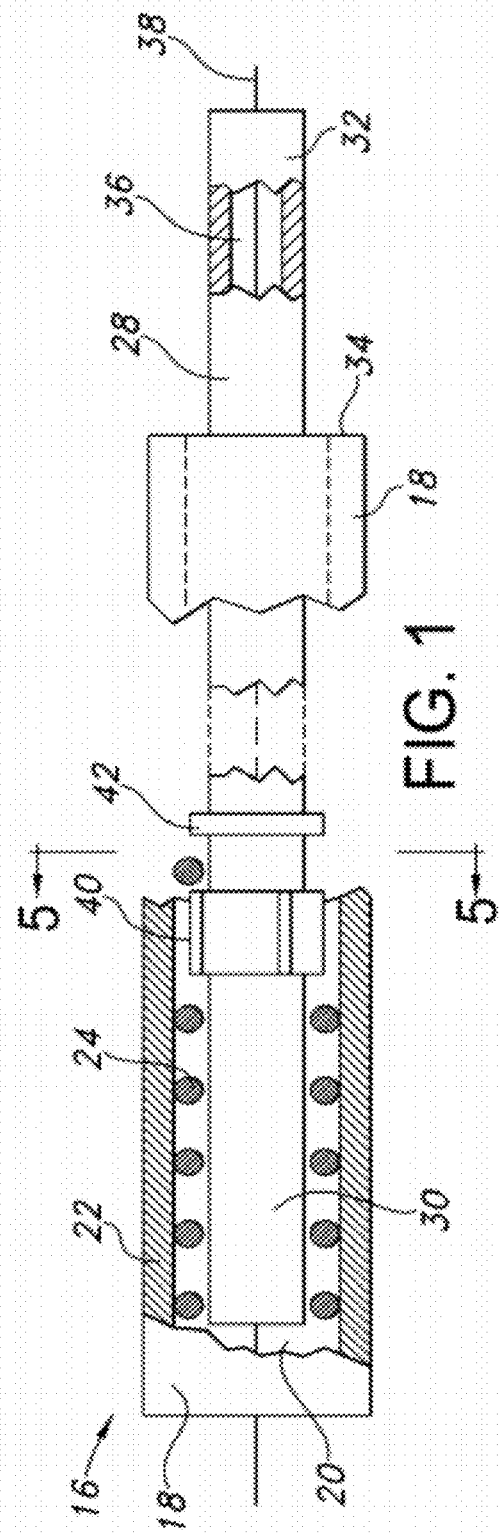
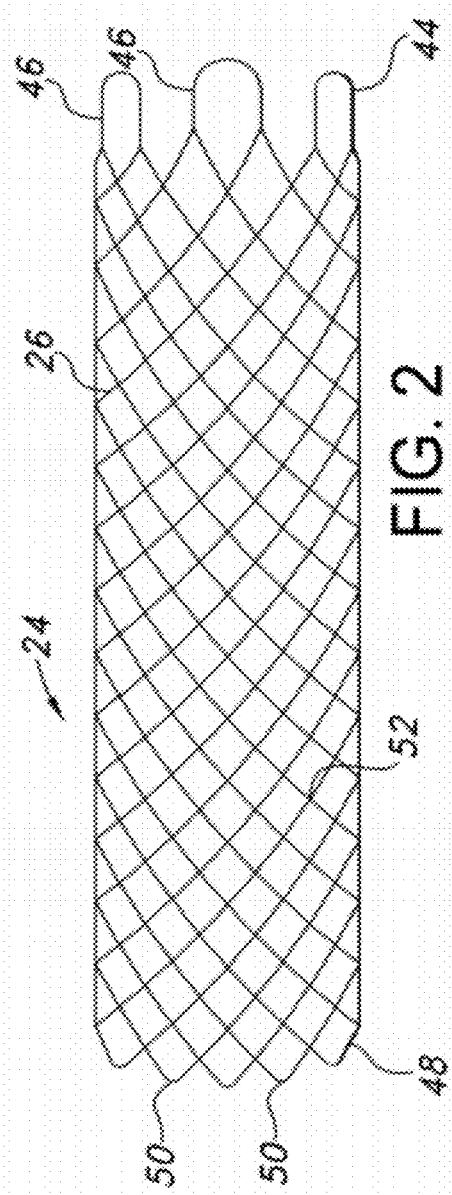
FIG. 1
FIG. 2

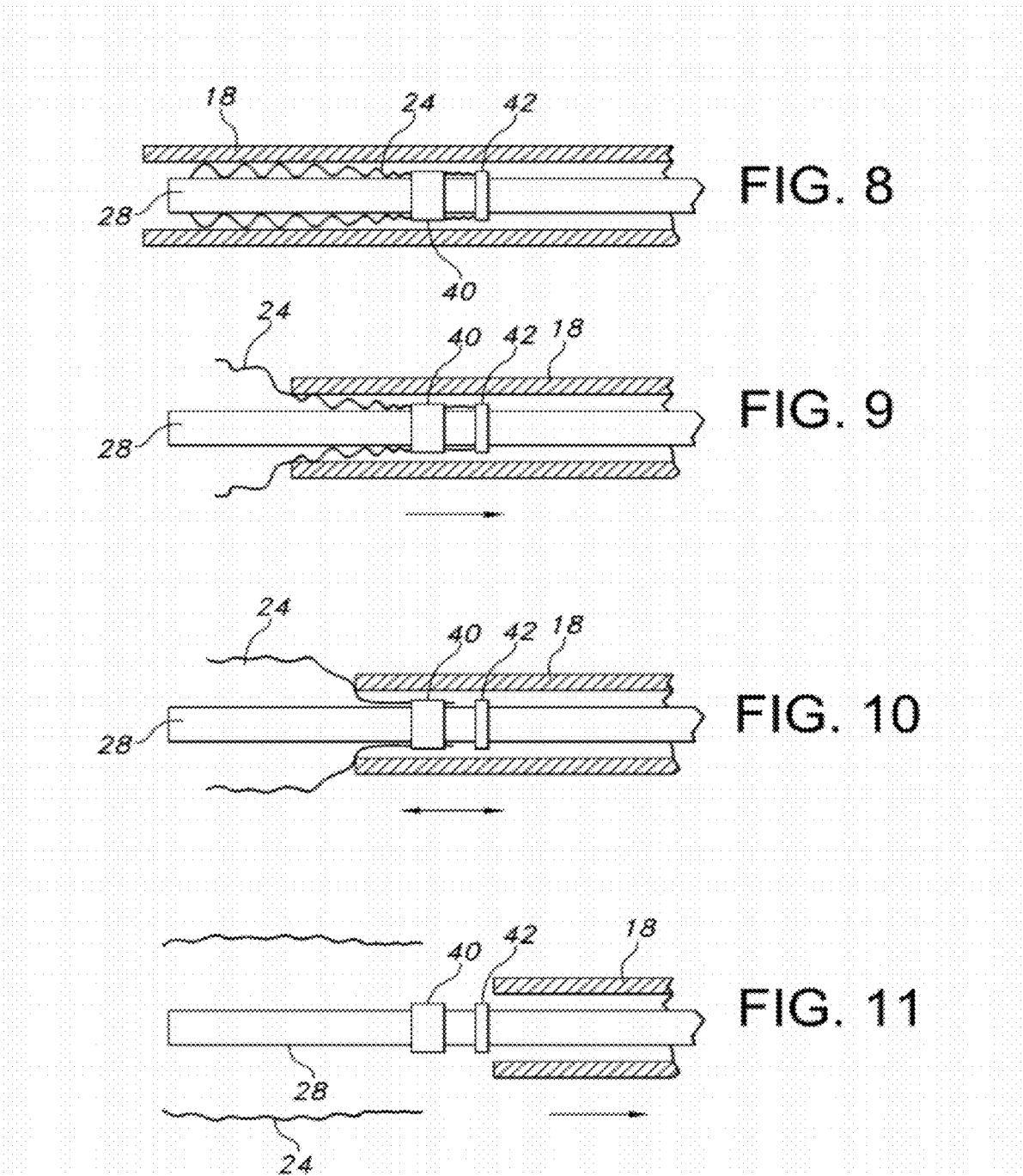

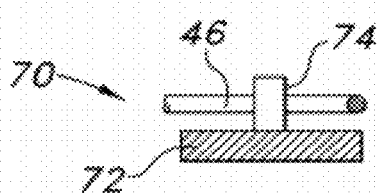
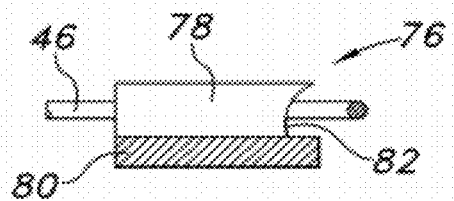
FIG. 12    FIG. 13
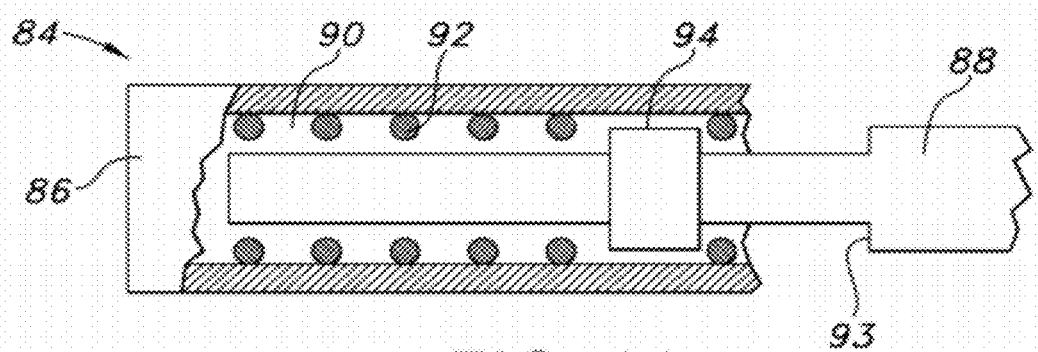
FIG. 14
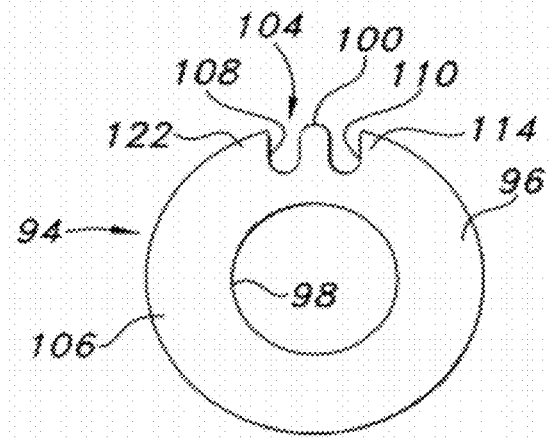
FIG. 15
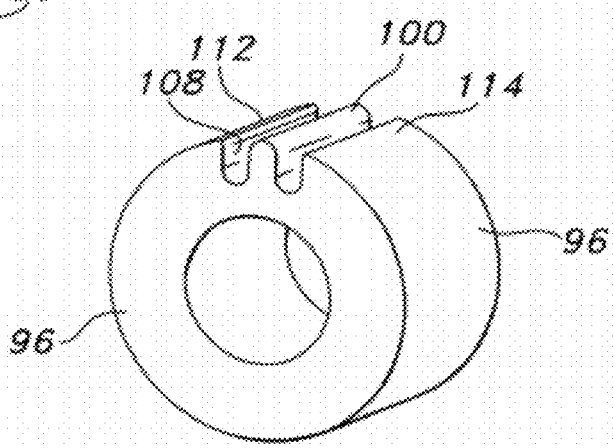
FIG. 16

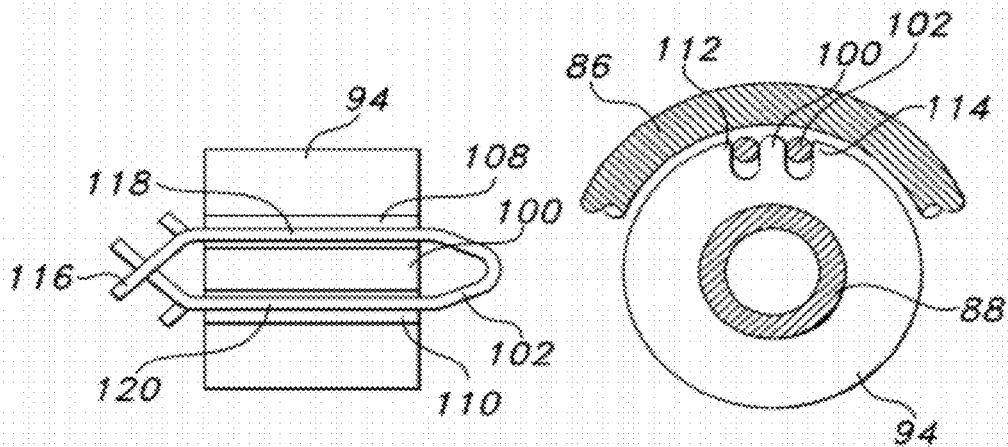
FIG. 17    FIG. 18
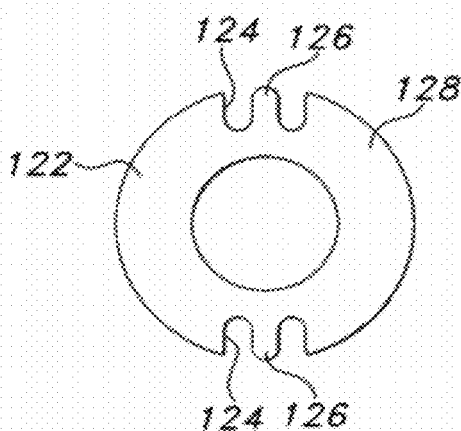    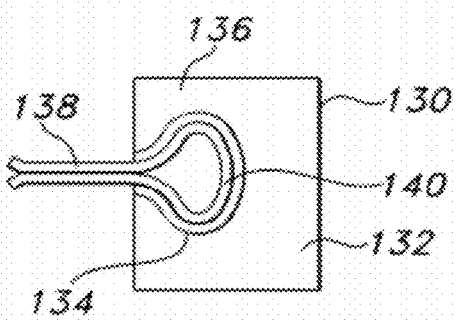
FIG. 19    FIG. 20

PROSTHESIS ANCHORING AND DEPLOYING DEVICE

BACKGROUND OF THE INVENTION

The present invention relates to systems for intraluminally delivering and deploying self-expanding stents and other prostheses, and more particularly to such systems that incorporate mechanisms for retrieving partially deployed prostheses.

Stents, stent-grafts, and other body implantable tubular devices are employed in a wide variety of applications to maintain the patency of body lumens and guide the flow of blood and other body fluids through the lumens. These devices are employed in vascular applications, e.g. in pulmonary and thoracic vessels, and in arteries such as the coronary, renal, carotid, and iliac arteries. In addition to these vascular applications, the devices are used in the esophagus, duodenum, biliary duct, and colon. These devices may be either radially self-expanding or balloon-expandable in character. When deployed within body lumens, self-expanding devices radially expand into contact with surrounding tissue, typically assuming a diameter less than a fully expanded or relaxed state diameter. Consequently, an internal elastic restoring force acts outwardly against the tissue to assist in fixation of the device. Self-expanding devices frequently are preferred, due to this self-fixation capability.

Most applications employing radially self-expanding devices require intraluminal delivery of the device in a configuration suitable for delivery, i.e. radially compressed to a reduced-radius state against its internal elastic restoring force. To this end, prosthesis delivery systems frequently include two catheters: an outer catheter releasably containing the radially compressed prosthesis in a lumen near its distal end, and an inner catheter contained in the lumen, positioned against or otherwise engaged with the prosthesis. The prosthesis is deployed by moving the outer catheter proximally while holding the inner catheter in place. This effectively moves the inner catheter and the prosthesis distally relative to the outer catheter, allowing the prosthesis to radially self-expand as it emerges from the distal end of the outer catheter.

In either event, there arises on occasion a need to reverse the deployment. The need may arise from the physician's desire to reposition the prosthesis along the intended treatment site. Once a substantial portion of the prosthesis is free of the outer catheter, it may be moved in the proximal direction. However, at this point it is virtually impossible to move the prosthesis in the distal direction without retracting it proximally, back into the outer catheter. Accurate positioning of the prosthesis during deployment is challenging, in that it usually requires fluoroscopic imaging, and the difficulty is increased by the tendency of the many self-expanding devices to axially shorten as they radially self-expand. The need to retract a prosthesis can arise from other factors, e.g. a realization during deployment that a prosthesis of a different axial length or radius would be more effective at the designated treatment site.

In many conventional deployment and delivery systems, retraction of a partially deployed prosthesis is virtually impossible. To provide a retractable prosthesis, an inner catheter or other member can be surrounded by a high friction sleeve or gripping member as shown in U.S. Pat. No. 5,026,377 (Burton et al.), with the portion of an inner catheter supporting the sleeve and surrounded by the prosthesis. When the outer catheter radially compresses the prosthesis, it simultaneously presses the prosthesis into a frictional engagement with the sleeve. Accordingly, when the outer catheter is moved relative to the inner catheter, the prosthesis tends to remain with the inner catheter rather than following the outer catheter. A similar approach is shown in U.S. Pat. No. 5,817,102 (Johnson et al.) in which an exterior catheter radially compresses a stent into contact with a restraining sleeve that surrounds an interior catheter.

While these arrangements permit proximal retraction of a partially deployed stent or other prosthesis, they rely on a frictional engagement of the prosthesis with the inner member, through the gripping member or restraining sleeve. The force due to the frictional engagement must be sufficient to overcome the tendency of the prosthesis to move with the outer catheter as the outer catheter moves relative to the inner member. This frictional force acts in the axial direction, but requires a force acting in the radial direction to urge the prosthesis against the gripping member. The required radial force adds to the radial force already exerted by the prosthesis against the outer catheter due to its internal elastic restoring force, thus to increase the axial pushing force required to overcome friction between the prosthesis and outer catheter, and deploy the prosthesis.

Another factor inherent in this approach is the reduction in the frictional holding force as prosthesis deployment progresses, largely due to the diminishing portion of the prosthesis length subject to the frictional hold. As deployment progresses, the prosthesis becomes increasingly easy to deploy. Conversely, when the prosthesis is being pulled back into the catheter to reconstrain it, the reconstrainment force increases as more and more of the prosthesis is pulled into the catheter. This tendency can be counteracted by increasing the frictional holding force, but this in turn increases the radial force required to overcome the frictional hold, once again increasing the force required for ordinary deployment.

Other arrangements involve axially tight or locking engagements of prostheses with inner member coupling structures. Examples of these arrangements are seen in U.S. Pat. No. 6,350,278 (Lenker et al.) and U.S. Pat. No. 5,733,325 (Robinson et al.). These systems permit prosthesis retraction, but impose unduly stringent tolerances upon the coupling structure. Further, they require close attention and care on the part of the physician or other user when loading a prosthesis into the system, to ensure that the required coupling is achieved.

Therefore, the present invention is disclosed in terms of several embodiments, each directed to at least one of the following objects:

to provide a prosthesis deployment system with the capability of retracting partially deployed prostheses, without any substantial increase in the axial forces required to deploy the prostheses;

to provide a prosthesis deployment system that permits retracting of the prosthesis at a later stage in its deployment, in terms of the fraction of the prosthesis axial length exposed, without degrading or losing retraction capability;

to provide a deployment device that has greater stent retention capability if the need arises for withdrawing a partially deployed stent;

to provide a deployment device capable of retracting partially deployed device in which an open-frame support structure is covered, e.g. as in stent-grafts; and to provide a prosthesis anchoring device suitable for attachment to an inner catheter or other inner member of a conventional prosthesis delivery and deployment system to provide the capability of retracting partially deployed prostheses.

SUMMARY OF THE INVENTION

To achieve these and other objects, there is provided a device for effecting an intraluminal delivery and controlled deployment of a body implantable prosthesis. The device includes an elongate prosthesis delivery member having a distal wall segment adapted to contain a radially self-expanding prosthesis in a reduced-radius delivery state against an internal restoring force. A radially self-expanding prosthesis is contained in the distal wall segment and thereby maintained in the reduced-radius delivery state. The prosthesis includes a linking structure near a proximal end of the prosthesis. An elongate prosthesis control member is mounted for axial travel relative to the delivery member, toward and away from a delivery position in which a distal end region of the control member extends along the distal wall segment of the delivery member and is disposed radially inwardly of the prosthesis. A control feature is disposed along the distal end region of the control member and extends radially outwardly from the control member beyond a radial midpoint of the linking structure when in the delivery position with the prosthesis so contained. Thus, the control feature is positioned to allow limited distal travel of the delivery member and prosthesis relative to the control member, and to effect a substantially non-frictional surface engagement with the linking structure upon said limited distal travel, to anchor the prosthesis against further distal travel relative to the control member.

The delivery member can comprise an outer catheter with a lumen running substantially along its complete length. The control member can comprise an elongate inner catheter disposed in the outer catheter lumen. Preferably a proximal region of the inner catheter extends beyond a proximal end of the outer catheter, to facilitate the use of the inner catheter proximal end to control the position of the inner catheter distal region relative to the outer catheter. This facilitates control of the prosthesis deployment from outside the body.

If desired, the control member can be provided with several control features, equally angularly spaced apart from each other about the control member, for use with a prosthesis in which the linking structure includes angularly spaced apart loops or other linking members. A one-to-one correspondence of control features and loops is workable, but not required. In one embodiment, three control features are used in conjunction with six loops formed at a proximal end of the prosthesis.

In a preferred embodiment, a tubular sleeve supports a symmetrical arrangement of control features, and is sized to facilitate its slideable installation onto the distal end region of the control member. The sleeve and control features are formed as a unitary member, preferably more rigid than the control member to provide more positive control over the prosthesis through engagement of the control features with the loops or other linking members. The control features can be surrounded by substantially closed loops of a prosthesis linking structure, in which case the features can control both proximal and distal prosthesis movement.

One aspect of the present invention is that the control feature outer ends define a control feature diameter less end than an inside diameter of the delivery member distal wall segment. At the same time, the radial spacing in between the control features and distal wall segment is less than half of a radial thickness dimension of the prosthesis linking structure. Consequently, the control member and control features are slideable relative to the delivery member with no frictional drag.

Yet, the control feature outer ends are sufficiently close to the distal wall section to prevent the linking structure or another part of the prosthesis from wedging into the space between the control features and distal wall segment.

A salient feature of the present invention is that the control member is operable to move the prosthesis proximally relative to the delivery device—or alternatively, to maintain the prosthesis substantially stationary while the delivery device is moved distally relative to the control member—through a surface engagement of each control feature with the prosthesis linking structure. The control features apply axial forces to the linking structure. Unlike the frictional prosthesis retraction systems discussed above, there is no need for frictional control of the prosthesis, and accordingly, no need for the additive radial force that undesirably increases the axial force required to deploy the prosthesis. Further, because the axial forces in the present system do not depend on friction, they do not diminish as prosthesis deployment progresses. As a result, the prosthesis can be fully retracted from a stage close to complete deployment, e.g. with up to ninety-five percent of its length positioned distally of the delivery device.

Another aspect of the present invention is a prosthesis delivery and deployment device. The device includes an elongate prosthesis delivery member having a distal wall segment adapted to contain a radially self-expanding prosthesis in a reduced-radius delivery state against an internal restoring force. An elongate control member is mounted for axial travel relative to the delivery member, toward and away from a delivery position in which a distal end region of the control member extends along the distal wall segment of the delivery member. A prosthesis anchor is mounted to the distal end region and comprises at least one elongate axially directed control feature extending radially outwardly from the control member. The control feature thereby is positioned to effect a releasable engagement with a proximal-end linking structure of a radially self-expanding prosthesis when in the delivery position and with the prosthesis so contained. The anchor, when in said engagement with the linking structure, is operable to anchor the prosthesis against distal travel relative to the control member.

Preferably, the anchor comprises a plurality of the elongate axially directed control features positioned to engage the linking structure. Then, the linking structure preferably includes a plurality of elongate axially directed loops, each associated with a different one of the control features. The anchor further can include a cylindrical anchoring body with a centrally located axial opening adapted to receive the control member and facilitate and mounting of the anchor in surrounding relation to the control member. The anchor advantageously can be more rigid than the control member, to provide a more positive engagement with its associated loop.

In one preferred version, the anchoring body has a recess directed inwardly from an outside surface of the anchoring body and adapted to receive a loop or other proximal-end linking structure of the prosthesis. The associated control feature is disposed in the recess, to be surrounded by the loop when the loop is received into the recess. In this version, the depth of the recess exceeds the radial thickness of the loop, so that the complete loop may be radially inwardly disposed relative to the outside surface.

A further aspect of the present invention is a prosthesis anchoring device adapted for fixation to a prosthesis deployment member. The device includes a generally cylindrical anchoring sleeve having a central opening extending axially therethrough to facilitate a slideable installation of the anchoring sleeve onto an elongate prosthesis deployment member for fixation along a distal end region of the deployment member. A control feature extends radially outwardly from the anchoring sleeve and is adapted to extend radially into a proximal-end linking structure of a radially self-expanding prosthesis when the prosthesis is maintained in a reduced-radius state against an internal restoring force and selectively axially aligned with the distal end region. The control feature, with the anchoring sleeve fixed to a deployment member and when so extending into a proximal-end linking structure of a radially self-expanding prosthesis so maintained and aligned, is adapted to engage the linking structure to prevent any substantial distal movement of the prosthesis relative to the deployment member.

Preferably, the control feature is elongate, directed axially, and adapted to extend into a prosthesis proximal-end linking structure taking the form of an elongate, axially extended loop. When surrounded by the loop, the control feature prevents any substantial distal movement of the loop relative to the anchoring body. In a more preferred version of the device, a plurality of the elongate control features are angularly spaced apart from one another about the anchoring body.

In another version of this device, the anchoring body includes a recess receding radially inwardly from its outside surface to receive the linking structure. The control feature is disposed within the recess. Typically, the depth of the recess exceeds the thickness of the linking structure. In systems that employ an outer catheter or other delivery device with a distal wall section designed to maintain a radially self-expandable prosthesis in a reduced-radius delivery state, the anchoring body can be dimensioned for a close fit within the distal wall section. As a result, the distal wall segment cooperates with the walls of the recess to capture the linking structure within the recess, while permitting the anchoring body to slide axially along the distal wall section.

To provide a more secure retention of the linking structure, the recess can be formed with a size and shape corresponding to that of the linking structure. For example, if the linking structure comprises an elongate linking strand formed into a loop, the recess can have a perimeter that closely corresponds to a perimeter of the loop. The control feature disposed in the recess is surrounded by the loop when the loop is retained in the recess. When surrounded by the loop, the control feature prevents any substantial distal movement of the loop relative to the anchoring body. As a result, the deployment member is operable through the anchoring body to deploy and retract the prosthesis.

In short, an anchoring body formed according to the present invention, with a central aperture sized according to a conventional prosthesis deployment catheter and with one or more control features sized according to the corresponding loops or other linking structure of a selected prosthesis, can considerably improve the prosthesis retraction capability of a prosthesis delivery and deployment system, without increasing the axial force required for deployment.

Several additional features enhance deployment system performance, regardless of whether the control features are recessed. For example, when the anchoring device is provided as a unitary structure including a cylindrical anchoring body and outwardly protruding control features, the device may be attached to a conventional inner catheter or other control member, fixed to the inner catheter at a location selected in accordance with the compressed length of the prosthesis to be deployed. Further, a relatively hard anchoring device can be fixed to a softer, more compliant inner catheter or control member, providing the capacity to negotiate serpentine internal passageways, while at the same time providing more positive control over the prosthesis through the relatively rigid control features.

Another useful feature arises from the provision of elongate control features and their axial orientation along the control member. This aligns the major dimension of each control feature with the direction of the forces applied through the control feature to the prosthesis, to overcome its tendency to follow the outer catheter or other prosthesis delivery member. As a result, the control features are more stable and less prone to unwanted flexure. The elongate axially directed features, as compared to pins or other features with circular cross sections, are better suited to limit twisting of the prosthesis relative to the control member. At the same time, the control features can have transverse widths selected to allow limited prosthesis rotation.

Yet another advantage arises from the positioning of each control feature to allow limited distal travel of the delivery member and prosthesis before the prosthesis engages the linking structure, and then to effect non-frictional surface engagement with the linking structure responsive to the limited distal travel. As compared to previous deployment systems with interlocks designed to prevent any axial movement of a prosthesis relative to an inner catheter or other control member, the novel coupling of the control feature and linking structure can be manufactured under tolerances that are less stringent. Further, loading the prosthesis into an outer catheter or other delivery member, while maintaining a prosthesis radially compressed and coupled to the control member through the control features, is much easier.

Yet another aspect of the present invention is a process for loading a radially self-expanding prosthesis for subsequent deployment in a body lumen, comprising the following steps:

a. positioning a radially self-expanding prosthesis along and in surrounding relation to a distal end region of an elongate prosthesis control member with a proximal end linking structure of the prosthesis disposed near axially spaced apart first and second features that extend radially outwardly from the control member;

b. with the prosthesis so positioned, radially contracting the prosthesis to a reduced-radius delivery state against an internal elastic restoring force, to move the linking structure into a delivery position between the first and second features, whereby the first and second features cooperate to limit axial travel of the prosthesis relative to the control member to a predetermined range so long as the prosthesis remains in the delivery state; and c. selecting an axial dimension of the linking structure with respect to an axial spacing between the first and second features whereby the predetermined range is at least twice the axial dimension of the linking structure.

Thus in accordance with the present invention, systems for intraluminally deploying radially self-expanding stents, stent-grafts and other implantable devices may be used to retract and withdraw such devices, even when deployment is near completion. There is no need for frictional retention of the device, and no resulting increase in axial force required for deployment. With the devices nearly deployed, yet retractable, physicians can evaluate prosthesis length, radius, placement relative to the treatment site, and other factors with more certainty as a basis for making critical decisions.

IN THE DRAWINGS

For a further understanding of the above and other features and advantages, reference is made to the following detailed description and to the drawings, in which:

FIG. 1 is a partial side elevation of a stent delivery and deployment system constructed in accordance with the present invention;

FIG. 2 is a side elevation of a radially self-expanding stent deployable with the system of FIG. 1;

Figures 6, 7:
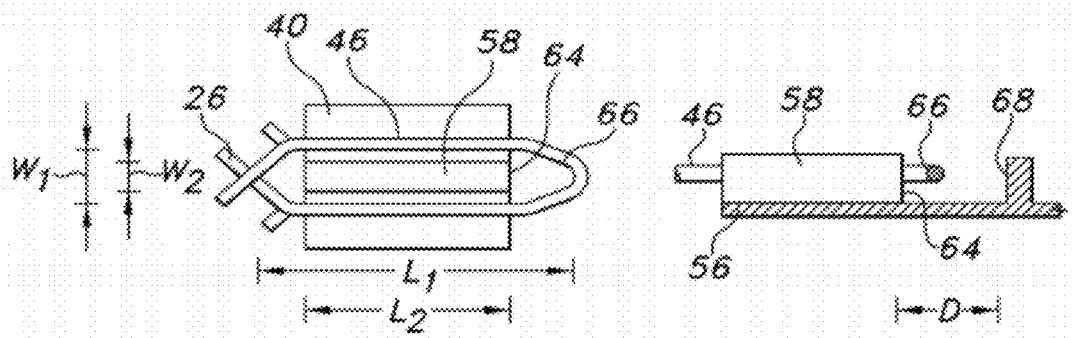
FIG. 6 is a schematic top view of a control feature of the anchoring device, surrounded by a loop of the stent.
FIG. 7 is a schematic side view, partially in section, of the control feature and loop.

FIGS. 8-11 schematically illustrate use of the system to deploy the stent;

FIG. 12 is a schematic view similar to that in FIG. 7, showing an alternative embodiment anchoring device;

FIG. 13 is a schematic view illustrating another alternative embodiment anchoring device;

FIG. 14 is a partial side elevation of an alternative embodiment stent delivery and deployment system constructed according to the present invention;

FIG. 15 is a forward elevation of a stent anchoring device employed in the system of FIG. 14;

FIG. 16 is a perspective view of the anchoring device;

FIG. 17 is a top view illustrating a loop of a radially self-expanding stent disposed in a recess of the anchoring device;

FIG. 18 is a forward elevation, partly in section, of the loop in the recess;

FIG. 19 is a forward elevation of an alternative embodiment stent anchoring device; and FIG. 20 is a top view illustrating another alternative embodiment anchoring device and stent linking member.

DETAILED DESCRIPTION OF THE PREFERRED EMBODIMENTS

Turning now to the drawings, there is shown in FIG. 1 a system 16 for intraluminally delivering and deploying a radially self-expanding stent, stent-graft, or other prosthesis. System 16 includes an elongate and pliable outer catheter 18 constructed of a biocompatible material such as polypropylene, FEP, HDPE, PTFE, or PET. A central lumen 20 runs the length of catheter 18. The tubular wall of catheter 18 includes a distal wall segment 22 containing a radially self-expanding stent 24. With reference to FIG. 2, stent 24 preferably is of open weave or mesh construction formed of multiple helically wound and braided filaments or strands 26 of a flexible material such as body compatible stainless steel. Other suitable materials include shape memory alloys such as Nitinol, or biocompatible polymers. Other filament configurations may be employed, including non-braided and non-helical configurations. Stent 24 is shown in a free or relaxed state, i.e. the state assumed by the stent when subject to no external force. Returning to FIG. 1, catheter 18 radially compresses stent 24, acting against an internal elastic restoring force of the stent to maintain the stent in an axially elongated, reduced-radius delivery state.

An elongate and pliable inner member or catheter 28 extends along a length of the outer catheter, contained in lumen 20. When system 16 is configured for stent delivery as shown in FIG. 1, a distal region 30 of inner catheter 28 is surrounded by the stent. Inner catheter 28 is movable axially relative to outer catheter 18. A proximal region 32 of the inner catheter extends proximally beyond a proximal end 34 of outer catheter 18, and is operable to control the axial position of distal region 30 relative to distal wall segment 22 of the outer catheter. Inner catheter 28 has an axially extending lumen 36 to accommodate a guidewire 38.

An anchoring device 40 is fixed in surrounding relation to inner catheter 28, near a proximal end of distal region 32. As is later explained, device 40 is operable to anchor stent 24 with respect to inner catheter 28, enabling use of the inner catheter to retract and recover a partially deployed stent.

A thrust member 42 is fixed in surrounding relation to inner catheter 28, proximally spaced apart from anchoring device 40. Inner catheter 28 is movable distally relative to outer catheter 18 to position thrust member 42 against the proximal end of stent 24, whereupon further distal travel of the inner catheter moves the stent distally relative to the outer catheter.

Inner catheter 28 is movable proximally relative to outer catheter 18 to bring anchoring device 40 into a surface engagement with stent 24. Alternatively, the inner catheter is movable distally to bring thrust member 42 into to surface contact with the stent. Thus, the inner catheter acts as a control member, to selectively control the position of stent 24 relative to the outer catheter.

As seen in FIG. 2, stent 24 has a proximal end 44 at which strands 26 are formed into a plurality of elongate loops 46. At a distal end 48 of the stent, the strands are formed into a plurality of bends 50. In this version, twenty-four helical windings, twelve in each of two opposite directions, form twelve of the distal end bends 50, and six proximal end loops 46. Loops 46 are equally angularly spaced apart about the stent periphery or circumference, in increments of sixty degrees from each loop to each adjacent loop. The optimal numbers of strands, loops and bends can differ, depending on the strand material and the procedure involved. The oppositely directed strands form multiple intersections or crossing points 52. The stent is shown in its relaxed state, when subject to no external stress.

Stent 24 is radially compressible, against an internal elastic restoring force, to an axially-elongated, reduced-radius delivery state. As seen in FIG. 1, distal wall segment 22 of the outer catheter provides the external force necessary to maintain stent 24 in the reduced-radius state, thus to facilitate the intraluminal delivery of the stent to the intended treatment site. When contained in this fashion, stent 24 exerts a radially outward force against distal wall segment 22 as a counter to the external force. This creates a frictional engagement of the stent and outer catheter, whereby the stent tends to follow proximal and distal movements of the outer catheter. Stent 24 is deployed through proximal movement of catheter 18 relative to inner catheter 28, with the inner catheter applying an axial (distal) force against the stent sufficient to overcome friction between the stent and outer catheter. This prevents the stent from moving proximally with the outer catheter. When free of outer catheter 18, stent 24 radially self-expands toward the relaxed state shown in FIG. 2.

In system 16, stent 24 closely surrounds but is not necessarily in contact with inner catheter 28. In contrast, in deployment systems that provide retraction through a frictional hold on the stent or other prosthesis, such contact not only is present, but must be maintained by exerting a radially inward force urging a stent against an inner catheter (or a sleeve or other gripping member along the inner catheter), to create a frictional hold that exceeds the frictional hold between the stent and the outer catheter. Thus, frictional systems provide for stent retraction, but at a cost: namely, a considerable increase in the axial force delivered by the inner catheter to deploy the stent. This is because the axial force must overcome not only the friction from the aforementioned restoring force of the stent, but the additional friction due to the additional radial force needed to press the stent against the inner catheter or gripping member. System 16, by providing an essentially non-frictional engagement of stent 24 with inner catheter 28, provides for stent retraction without increasing the axial force needed to deploy the stent.

Figures 3, 4:
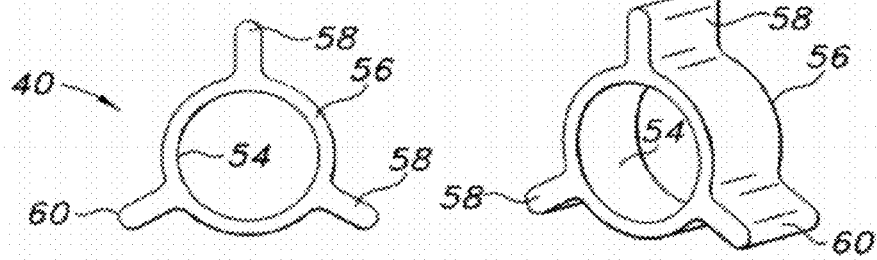
FIG. 3 is a forward elevation of a stent anchoring device employed in the system of FIG. 1.
FIG. 4 is a perspective view of the anchoring device.

As seen in FIG. 1, when stent 24 is radially compressed in the delivery state, it is releasably coupled to inner catheter 28 through anchoring device 40. With reference to FIG. 3, anchoring device 40 is symmetrical about a longitudinal axis. A central opening 54 extends through the device, and has a diameter slightly larger than the outside diameter of inner catheter 28 at least along the distal region. This provides a slideable fit, to facilitate installation of the anchoring device onto the inner catheter, where the device can be fixed at its intended location by an adhesive, thermal processing, ultrasonic welding or other suitable approach. Anchoring device 40 includes a longitudinally extending sleeve 56. Three splines or fins 58 extend longitudinally along sleeve 56 and radially outward from the sleeve, to respective radially outward ends 60.

Anchoring device 40 preferably is a unitary member, formed of a polymer such as ABS, polycarbonate, or nylon 12. Thus, it can be harder or more rigid than inner catheter 28 and outer catheter 18. As a result, the anchoring device when engaged with stent 24 through loops 46 can more positively anchor and otherwise control the position of the stent.

Figure 5:
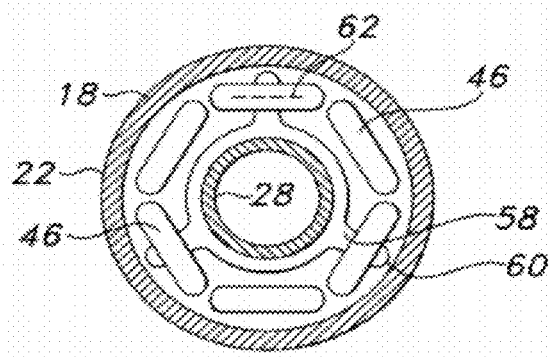
FIG. 5 is a sectional view taken along the line 5-5 in FIG. 1.

The nature of the coupling between anchoring device 40 and stent 24 is best understood with reference to FIGS. 5-7. As best seen in FIG. 5, each of fins 58 extends through one of loops 46, to a point beyond its associated loop and just inside of distal wall segment 22. Preferably, an outer diameter defined by outward ends 60 is less than the inside diameter of the distal wall segment by an amount less than the radial thickness of loops 46, i.e. the diameter of strands 26. The result is that in a coaxial arrangement, the radial spacing between each end 60 and the distal wall segment is less than one-half the strand diameter. This arrangement ensures a positive retention of each loop about its associated fin.

In a satisfactory but less preferred arrangement, each fin extends radially to position its outer end beyond a radial midpoint of its associated loop, i.e. beyond the geometric center of strand 26 as indicated by the broken line at 62.

In FIG. 5, loops 46 are shown spaced apart inwardly from the distal wall segment. This is partly for convenience in illustrating the positional relationship between each fin and its associated loop. Further, at least a portion of each loop is spaced apart from the distal wall segment, by virtue of the fact that the profile of each loop as viewed in FIG. 5 extends as a chord in relation to the circular profile of wall segment 22. Finally, this figure illustrates that there need not be a one-to-one correspondence of fins to loops, although it is preferable to have a symmetrical arrangement in which the number of loops is an integral multiple of the number of fins, as shown.

FIGS. 6 and 7 illustrate one of loops 46 surrounding its associated fin 58. As shown in FIG. 6, fin 58 has a transverse width less than the corresponding interior width of loop 46. Alternatively, fin 58 can be tapered, with a width that increases in the radially inward direction, so that the loop tends to engage the opposite sides of the fin as it is placed onto the fin. In either event, fin 58 is positioned for limited axial travel within the associated loop. When outer catheter 18 is moved distally relative to inner catheter 28, loop 46 follows the outer catheter and moves distally (to the left as viewed in FIGS. 6 and 7) until a proximal end surface 64 of the fin engages a proximal inside surface 66 of loop 46. The remaining two fins similarly engage proximal inside surfaces of their associated loops. Once the loops and fins are engaged, device 40 functions as an anchor that prevents further distal movement of stent 24, despite further distal travel of the outer catheter. The proximal end surfaces of fins 58 extend radially, so that together they occupy a plane perpendicular to the axial direction. This promotes the anchoring function, particularly when the strand forming loop 46 has a circular profile or cross section.

It is preferred to couple fin 58 and loop 46 as shown, to allow limited relative axial travel. As an alternative, the fin and loop could be configured to form a close or tight coupling that would virtually prevent relative axial movement of the stent and inner catheter. The looser, more flexible coupling has several advantages. The loops and fins can be formed under less demanding tolerances. Further, with the more flexible coupling it is much easier for the physician to load stent 24 into outer catheter 18 while maintaining the stent position relative to inner catheter 28.

As perhaps best seen in FIG. 6, loops 46 and fins 58 are elongate in the axial direction. Thus, the major dimension of the fin coincides with the direction of forces applied to the loop through the fin. Further, fin 58 cooperates with the opposite axially extending sides of loop 46 to provide a more stable coupling of the loop and fin that not only limits relative axial travel, but also resists twisting of the stent relative to the inner catheter, even when allowing limited relative rotation to provide the advantages of less stringent tolerances and ease of stent loading.

Preferably a distance D between end surface 64 of the fin and an end surface 68 of the thrust member is selected in conjunction with a diameter d of strand 26 forming the loop, to determine a range of axial travel of stent 24 relative to inner catheter 28. In exemplary embodiments, distance D is from 1 mm to 2 mm and diameter d is 0.3 mm. The resulting range of axial travel is 0.7 mm to 1.7 mm, or in terms of the ratio D/d, is from 3.3 to 6.7. Advantageously, the ratio D/d is at least about 2.

Further, an axial length $L_1$ of the interior of loop 46 exceeds an axial length $L_2$ of fin 58 sufficiently to permit the required freedom of axial movement of the fin within the loop. For example, $L_1$ can be 5.5 mm, with $L_2$ being 3-4 mm. To allow limited rotation or transverse movement of the prosthesis relative to the inner catheter, an internal transverse width $W_1$ of loop 46 exceeds a transverse width $W_2$ of the fin. More specifically, $W_1$ can be 1.5 mm and $W_2$ can be 0.3 mm. Advantageously, $W_1$ is at least about twice $W_2$.

The use of anchoring device 40 to control stent deployment is illustrated in FIGS. 8-11. In FIG. 8, stent 24 surrounds the distal region of inner catheter 28, radially compressed in the reduced-radius delivery state by outer catheter 18. Typically, stent 24 is loaded into this position first by placing the stent in its relaxed state around the distal end region of the inner catheter, with loops 46 axially aligned with anchoring device 40. Then stent 24, at least along its proximal end near the loops, is elongated axially and radially reduced sufficiently to bring three of the loops about the three fins. The inner catheter and stent are moved proximally into the outer catheter, until the distal wall segment completely surrounds the stent, as shown in FIG. 8. At this point, system 16 is inserted into the body and moved distally along a vessel or other body lumen, until the distal ends of the catheters are positioned near the intended treatment site. The catheters are moved distally over a previously positioned guidewire, not shown.

At this stage, the user controls the proximal ends of the catheters, holding inner catheter 28 substantially stationary while proximally withdrawing outer catheter 18. Thrust member 42 engages stent 24 to prevent further proximal movement of the stent, in effect moving the stent distally relative to the outer catheter. As the stent emerges from the distal end of the outer catheter, it radially self-expands toward its relaxed state, as seen in FIG. 9. The arrow indicates proximal movement of the outer catheter.

As depicted in FIG. 10, outer catheter 18 is moved proximally a sufficient distance to nearly complete the deployment of stent 24. Over at least about half of its length, the stent has radially expanded into contact with surrounding tissue (not shown) at the treatment site. The arrow indicates that at this stage, outer catheter 18 may be moved in either axial direction, depending on the physician's determination of factors critical to the implantation procedure; e.g. whether the stent is properly positioned, and whether the stent has a diameter and axial length appropriate for the procedure. In practice, stent 24 may remain retractable with up to ninety-five percent of its length disposed distally of outer catheter 18.

If the stent is properly positioned, and the earlier determinations as to stent size are confirmed, outer catheter 18 is moved further in the proximal direction, to completely release stent 24 for full radial expansion into contact with surrounding tissue, as indicated in FIG. 11. At this point, catheters 18 and 28 are withdrawn.

Conversely, if stent 24 needs to be repositioned or replaced, outer catheter 18 is moved distally to recompress and recapture the stent, restoring the configuration shown in FIG. 8. Then, catheters 18 and 28 are moved in concert to reposition the stent, or are withdrawn to allow substitution of another stent.

Several advantages of system 16, as compared to retraction devices that rely on friction, can be appreciated in conjunction with FIGS. 8-11. The first of these is lower axial deployment force. Anchoring device 40, unlike friction-based devices, adds nothing to the axial force needed to maintain inner catheter 28 and stent 24 in place while proximally withdrawing outer catheter 18. Likewise, this approach adds nothing to the axial force needed to retract a partially deployed stent.

Moreover, the coupling of stent 24 to inner catheter 28 through the anchoring device provides substantially the same anchoring force, regardless of the extent of stent deployment. Unlike friction-based systems, the amount of axial holding force available to retract the stent does not diminish as deployment progresses. Thus, the physician can deploy stent 24 to a point of near completion as indicated in FIG. 10, confident that anchoring device 40 remains capable of retracting the stent if necessary. More accurate determinations relating to stent placement and size can be made with stent 24 at a stage close to full stage deployment as in FIG. 10. As compared to the partial deployment stage indicated in FIG. 9, or conventional designs that allow only partial deployment, the configuration in FIG. 10 provides a better basis for making critical decisions regarding stent size and placement.

FIG. 12 illustrates part of an alternate embodiment anchoring device 70 including a sleeve 72 and a plurality of pins extended radially away from the sleeve, one of which is shown at 74. When stent 24 is constrained to the reduced-radius state, pin 74 extends through one of loops 46 or an opening in the stent lattice structure in the same manner as fin 58, while permitting a wider latitude of axial movement of the loop relative to the anchoring device. This approach may be more suitable to a prosthesis that has less columnar strength.

FIG. 13 shows a portion of another alternative anchoring device 76 in which several fins, one of which is shown at 78, extend radially away from a sleeve 80. A proximal end surface 82 of the fin is concave in the proximal direction. Consequently, when stent 24 is moved distally relative to the anchoring device, fins 78 function as hooks to more positively capture their associated loops. The capturing function can be achieved through other profiles in end surface 82, e.g. profiles with notches, slots, and other suitable depressions or concavities. As a further alternative, end surface 82 can be inclined proximally as it extends radially outward to capture the associated loop.

FIG. 14 illustrates a distal portion of an alternative embodiment prosthesis delivery and deployment system 84, including an outer catheter 86, an inner catheter 88 contained in a lumen 90 of the outer catheter for axial travel relative to the outer catheter, and a radially self-expanding stent 92 contained in a reduced-radius state along a distal wall segment of the outer catheter. A cylindrical anchoring device 94 is secured to the inner catheter, and is releasably engaged with a loop 96 at the proximal end of stent 92. In lieu of a thrust member (e.g. 42), catheter 88 is formed with a shoulder 93 to provide the thrust member or feature.

As seen in FIGS. 15 and 16, anchoring device 94 includes a cylindrical body 96, with an opening 98 extending axially through the body to facilitate installation and mounting of the anchoring device along a distal end region of inner catheter 88. Anchoring device 94 is shaped to provide a control feature, specifically a medial feature 100, that interacts with a loop 102 of stent 92 in much the same manner as fin 58 interacts with loop 46. However, body 96 further is shaped to provide a recess 104 directed radially inwardly from an annular outside surface 106 of the body. Medial feature 100 extends radially outwardly from an inside central portion of the recess, in effect forming axially directed grooves or recess segments 108 and 110 between feature 100 and side features 112 and 114, respectively.

FIGS. 17 and 18 illustrate loop 102 retained releasably within the recess. A strand 116 forming the loop includes spaced apart longitudinal sections 118 and 120, retained respectively in grooves 108 and 110. The outside diameter of body 96 is less than an inside diameter of catheter 86 along the distal wall segment, to enable the anchoring member to slide relative to the outer catheter. Also, the difference between the body diameter and the inside diameter of the distal wall segment is less than the diameter of strand 116, to ensure that loop 102 is positively retained in recess 104, so long as the proximal portion of the prosthesis near loop 102 remains radially compressed.

FIG. 19 illustrates an alternative embodiment anchoring member 122, with recesses 124 and medial features 126 formed along opposite sides of a cylindrical body 128. Device 122 can be used with the single-loop stent shown in FIG. 14, or with a stent having two opposed proximal end loops. Thus, the number of recess/medial feature combinations can exceed the number of loops, but must at least equal the number of loops to accommodate all loops, due to the close spacing between body 128 and the outer catheter.

In anchoring device 94, medial feature 100 and loop 102 form a coupling that is asymmetrical, in the sense that the axial force does not act through a central axis of the anchoring device. Nonetheless, the narrow spacing between outside surface 106 and the inside surface of outer catheter 86 facilitates a smooth sliding movement of inner catheter 88 within the outer catheter. In contrast, anchoring member 122 provides a symmetrical arrangement with a more balanced application of axial forces. In either arrangement, the number of recesses can be equal to, or an integral multiple of, the number of loops.

An advantage of anchoring devices 94 and 122, as compared to anchoring devices without recesses, is that they can more easily accommodate covered devices such as stent-grafts. This is because medial features 100 and 126 do not extend beyond the outer surfaces of their respective anchoring bodies, and thus do not interfere with a graft or other covering surrounding the stent.

FIG. 20 illustrates another alternative embodiment anchoring device 130 with a cylindrical anchoring body 132 and a recess 134 directed radially inwardly from an annular outside surface 136 of the body. A filament or strand 138 of a stent (not fully shown) is shaped into a loop or other linking member 140 at the proximal end of the stent. Recess 134 has a shape corresponding to the profile of loop 140, with a radially oriented recess wall that substantially surrounds the loop. The recess wall functions as the control feature, Consequently, so long as the stent is maintained in a reduced-radius state, anchoring device 130, through surface engagement with loop 140, can anchor the stent alternatively against proximal and distal movement relative to anchoring device 130 and its associated inner catheter.

While loop 140 provides a convenient proximal end linking member of a stent, it is apparent from FIG. 20 that a bend, twist, or other enlargement formed in strand 138 can provide a suitable surface engagement with body 132 when captured within recess 134. Further, strand 138 may include adjacent portions twisted together, yet terminating in a loop similar to loop 140. Looped ends are generally favored, due to their atraumatic character. As with previous embodiments, the stent linking structure can consist of a single loop or other linking member, or a plurality of linking loops or members arranged angularly about the stent.

Thus in accordance with the present invention, stents and other prostheses of the radially self-expanding type are deployable at relatively low levels of axial force, and further are retrievable at multiple stages of deployment. Inner catheters or other inner members are provided with anchoring devices that have radially extending fins, recesses, or other features designed to interact with loops or other proximal-end linking members of prostheses, to anchor the prostheses through surface-to-surface engagement rather than friction, thus to provide more positive anchoring without the need for any additional axial force for prosthesis deployment or retraction.

What is claimed is:

1. A device for effecting an intraluminal delivery and controlled deployment of a body implantable prosthesis, comprising:
    an elongate prosthesis delivery member having a distal wall segment containing a radially self-expanding prosthesis in a reduced-radius delivery state against an internal restoring force;
    the radially self-expanding prosthesis contained in the distal wall segment and thereby maintained in the reduced-radius delivery state, said prosthesis including a plurality of helically wound strands interbraided to define an open tubular frame structure having a proximal end and a distal end, wherein the strands at the distal end are formed into a plurality of bends and wherein the strands at the proximal end are formed into a plurality of axially elongated loops having a strand crossing point and having a greater longitudinal extent than a distance between adjacent strand crossings within the frame structure of the prosthesis to define a linking structure at the proximal end of the prosthesis thereat, each of the plurality of axially elongated loops having spaced apart longitudinal sections formed from a monofilament strand, wherein each of said plurality of axially elongated loops includes two of said plurality of helically wound strands integrated into said monofilament strand of each of said longitudinal sections;
    an elongate prosthesis control member mounted for axial travel relative to the delivery member, toward and away from a delivery position in which a distal end region of the control member extends along the distal wall segment of the delivery member and is disposed radially inwardly of the prosthesis;
    a control feature comprising a cylindrical body having an annular outside surface, said annular outside surface having a plurality of recesses directed radially inward from the annular outside surface to form axially directed recess segments having recess walls, wherein the recess walls of pairs of the axially directed recess segments substantially surround said monofilament strand of the spaced apart longitudinal sections of the axially elongated loops of the prosthesis such that medial portions of the cylindrical body between the pairs of axially directed recess segments extend into the elongate loops, wherein only said monofilament strand of said longitudinal sections extends within the recess walls of the pairs of the axially directed recess segments, the cylindrical body being disposed along the distal end region of the control member and extending radially outwardly from the control member beyond a radial midpoint of the linking structure when in the delivery position with the prosthesis so contained, thereby being positioned to allow limited distal travel of the delivery member and prosthesis relative to the control member, and to effect a substantially non-frictional surface engagement with the linking structure upon said distal travel, and
    a thrust feature disposed along the control member and surrounding said control member, spaced apart proximally from the control feature, and positioned to allow limited proximal travel of the delivery member and prosthesis relative to the control member when in the delivery position with the prosthesis so contained, and to engage the proximal end of the prosthesis responsive to said limited proximal travel and thereby prevent further proximal travel of the prosthesis relative to the control member.

2. The device of claim 1 wherein:
the distal end region is surrounded by the prosthesis when in said delivery position.

3. The device of claim 1 wherein:
the delivery member comprises an elongate outer catheter having a lumen running substantially the entire length of the outer catheter.

4. The device of claim 3 wherein:
the control member comprises an elongate inner catheter disposed in said lumen, wherein a proximal region of the inner catheter extends proximally beyond a proximal end of the outer catheter to facilitate use of the proximal region to control a position of the distal end region relative to the outer catheter.

5. The device of claim 1 wherein:
said control feature is formed as a unitary member.

6. The device of claim 1 wherein:
the linking structure has an axial dimension along a portion thereof disposed between the thrust feature and the control feature when the prosthesis is so contained, and an axial spacing between the thrust feature and the control feature is selected to determine a range, for axial travel of the prosthesis relative to the control member, of 3.3 to 6.7 times said axial dimension.

7. The device of claim 6 wherein:
said range for axial travel is at least about 0.7 mm and at most about 1.7 mm.

8. The device of claim 1 wherein:
a radial self-expansion of the prosthesis upon its release from the delivery member carries the linking structure radially outward beyond the control feature, thus to disengage the prosthesis from the control member.

9. A prosthesis delivery and deployment device, comprising:
an elongate prosthesis delivery member having a distal wall segment containing a radially self-expanding prosthesis in a reduced-radius delivery state against an internal restoring force;
said radially self-expanding prosthesis contained in the distal wall segment and thereby maintained in the reduced-radius delivery state, said prosthesis including a plurality of helically wound strands interbraided to define an open tubular frame structure having a proximal end and a distal end, wherein the strands at the distal end are formed into a plurality of bends and wherein the strands at the proximal end are formed into a plurality of axially elongated loops having a strand crossing point and having a greater longitudinal extent than a distance between adjacent strand crossings within the frame structure of the prosthesis to define a linking structure at the proximal end of the prosthesis thereat, each of the plurality of axially elongated loops is formed from a monofilament strand, said monofilament strand having spaced apart longitudinal sections;
an elongate prosthesis control member mounted for axial travel relative to the delivery member, toward and away from a delivery position in which a distal end region of the control member extends along the distal wall segment of the delivery member and is disposed radially inwardly of the prosthesis; and
a control feature comprising a cylindrical body having an annular outside surface, said annular outside surface having a plurality of recesses directed radially inward from the annular outside surface to form axially directed recess segments having recess walls a medial portion extends from each of said plurality of recesses, wherein only said monofilament strand extends between said recess wall and said medial portion, the cylindrical body being disposed along the distal end region of the control member and extending radially outwardly from the control member beyond a radial midpoint of the linking structure when in the delivery position with the prosthesis so contained, thereby being positioned to allow limited distal travel of the delivery member and prosthesis relative to the control member, and to effect a substantially non-frictional surface engagement with the linking structure upon said distal travel;
wherein said medial portions are elongate axially directed fins, said fins being tapered wherein a width of each of said fins decrease as the fins extend radially outward and thereby positioned to effect a releasable engagement with the proximal-end linking structure of the radially self-expanding prosthesis and to engage opposite sides of the plurality of the axially elongated loops when in the delivery position and with the prosthesis so contained.

10. The device of claim 9 further including:
a thrust feature mounted to the control member proximally of the control feature and operable, through proximal travel of the delivery member relative to the control member with the prosthesis so contained, to establish surface contact with the linking structure to anchor the prosthesis against further proximal movement relative to the control member.

11. The device of claim 10 wherein:
the linking structure has an axial dimension along a portion thereof disposed between the control feature and the thrust feature when the prosthesis is so contained; and
an axial spacing between the control feature and the thrust feature is selected to determine a range, for axial travel of the prosthesis relative to the control member, of 3.3 to 6.7 times the axial dimension.

12. The device of claim 11 wherein:
said range is at least about 0.7 mm and at most about 1.7 mm.

13. The device of claim 9 wherein:
said recesses are directed inwardly a distance greater than a radial thickness dimension of the loop.

14. The device of claim 9 wherein:
the distal end region is surrounded by the prosthesis when in said delivery position.

15. The device of claim 9 wherein:
the delivery member comprises an elongate outer catheter having a lumen running substantially the entire length of the outer catheter.

16. The device of claim 15 wherein:
the control member comprises an elongate inner catheter disposed in said lumen, with a proximal region of the inner catheter extending proximally beyond a proximal end of the outer catheter to facilitate use of the proximal region to control a position of the distal region relative to the outer catheter.

17. The device of claim 9 wherein:
the cylindrical body comprises a centrally located axial opening therethrough adapted to receive the control member and facilitate a mounting of the control feature in surrounding relation to the control member.

18. A process for loading a radially self-expanding prosthesis for subsequent deployment in a body lumen, including:
providing a radially self-expanding prosthesis comprising a plurality of helically wound strands interbraided to define an open tubular frame structure having a proximal end and a distal end, wherein the strands at the distal end are formed into a plurality of bends and wherein the strands at the proximal end are formed into a plurality of axially elongated loops having a strand crossing point and having spaced apart longitudinal sections and having a greater longitudinal extent than a distance between adjacent strand crossings within said frame structure of the prosthesis to define a proximal-end linking structure of the radially self-expanding prosthesis thereat, wherein each of said plurality of axially elongated loops includes two of said plurality of helically wound strands integrated into a monofilament strand defining each of said longitudinal sections;
positioning the radially self-expanding prosthesis along and in surrounding relation to a distal end region of an elongate prosthesis control member, wherein the control member comprises a cylindrical body having an annular outside surface, said annular outside surface having a plurality of recesses directed radially inward from the annular outside surface to form axially directed recess segments having recess walls, wherein the recess walls of pairs of the axially directed recess segments substantially surround said monofilament strand of each of the spaced apart longitudinal sections of the axially elongated loops of the prosthesis such that medial portions of the cylindrical body between the pairs of axially directed recess segments extend into the elongate loops, wherein said monofilament strand of said each of said longitudinal sections extends within each of the recess walls of the pairs of the axially directed recess segments; and with the prosthesis so positioned, radially contracting the prosthesis to a reduced-radius delivery state against an internal elastic restoring force to move the linking structure into a delivery position, wherein a width of said each of said plurality of axially elongated loops between said at least two of said plurality of helically wound strands is at least about twice a width of the medial portions of the cylindrical body.

19. The process of claim 18 wherein:

radially contracting the prosthesis comprises progressively advancing a prosthesis delivery member over the prosthesis to contain the prosthesis in the delivery state within a lumen of the delivery member.

\* \* \* \* \*

UNITED STATES PATENT AND TRADEMARK OFFICE
CERTIFICATE OF CORRECTION

| | |
|---|---|
| PATENT NO. | : 8,337,543 B2 |
| APPLICATION NO. | : 10/982465 |
| DATED | : December 25, 2012 |
| INVENTOR(S) | : Gary Jordan et al. |

It is certified that error appears in the above-identified patent and that said Letters Patent is hereby corrected as shown below:

In the Specifications

Column 16, Line 28, insert --end-- between "distal" and "region".

Signed and Sealed this
Seventh Day of May, 2013

Teresa Stanek Rea
*Acting Director of the United States Patent and Trademark Office*